United States Patent [19]
Vandervalk

[11] Patent Number: 5,979,241
[45] Date of Patent: Nov. 9, 1999

[54] DELAY LINE FOR AN ULTRASONIC PROBE AND METHOD OF USING SAME

[75] Inventor: Leon C. Vandervalk, Ontario, Canada

[73] Assignee: DeFelsko Corporation, Ogdensburg, N.Y.

[21] Appl. No.: 09/054,486

[22] Filed: Apr. 3, 1998

Related U.S. Application Data

[62] Division of application No. 08/392,507, Feb. 23, 1995, Pat. No. 5,777,230.

[51] Int. Cl.⁶ .................................................. G01N 29/24
[52] U.S. Cl. ............................................. 73/644; 73/1.82
[58] Field of Search .................................. 73/1.82, 1.86, 73/597, 598, 602, 629, 632, 642, 644, 661

[56] References Cited

U.S. PATENT DOCUMENTS

| | | |
|---|---|---|
| 3,237,251 | 3/1966 | Thalman . |
| 3,427,866 | 2/1969 | Weighart . |
| 3,486,368 | 12/1969 | Brech . |
| 3,554,013 | 1/1971 | Berg . |
| 3,663,842 | 5/1972 | Miller . |
| 3,690,154 | 9/1972 | Wells . |
| 3,918,296 | 11/1975 | Kitada . |
| 4,016,530 | 4/1977 | Goll . |
| 4,050,292 | 9/1977 | Bloch . |
| 4,100,808 | 7/1978 | Evans . |
| 4,102,205 | 7/1978 | Pies et al. . |
| 4,153,894 | 5/1979 | Alphonse et al. . |
| 4,182,155 | 1/1980 | Fowler . |
| 4,324,141 | 4/1982 | Stearn . |
| 4,366,406 | 12/1982 | Smith . |
| 4,383,194 | 5/1983 | Ohigashi et al. . |
| 4,393,711 | 7/1983 | Lapides . |
| 4,437,332 | 3/1984 | Pittaro ........................................ 73/597 |
| 4,445,360 | 5/1984 | Treder, Jr. . |
| 4,567,747 | 2/1986 | Matay . |
| 4,715,008 | 12/1987 | Jones . |
| 4,738,131 | 4/1988 | Euverard . |
| 4,756,808 | 7/1988 | Utsumi et al. . |
| 4,771,205 | 9/1988 | Mequio . |
| 4,961,347 | 10/1990 | Arakawa et al. . |
| 5,095,754 | 3/1992 | Hsu et al. ................................. 73/602 |
| 5,156,636 | 10/1992 | Kuljis . |

FOREIGN PATENT DOCUMENTS

| | | |
|---|---|---|
| 0130709 | 1/1985 | European Pat. Off. . |
| 0210723 | 2/1987 | European Pat. Off. . |
| 1121523 | 7/1968 | United Kingdom . |
| 1171377 | 11/1969 | United Kingdom . |
| 1541250 | 2/1979 | United Kingdom . |
| 2 040 048 | 8/1980 | United Kingdom . |
| 2109555 | 6/1983 | United Kingdom . |

OTHER PUBLICATIONS

Krautkramer, J., et al. Ultrasonic Testing of Materials, N.Y., Springer–Vertag, 1983. p. 620, Table A.1.

McMaster, R.C. Nondestructive Testing Handbook, N.Y., The Ronald Press Co., 1959. pp. 43–48 (no month).

*Primary Examiner*—Christine K. Oda
*Attorney, Agent, or Firm*—Burns, Doane, Swecker & Mathis, L.L.P.

[57] ABSTRACT

An ultrasonic probe includes an ultrasonic transducer; a delay line acoustically coupled to the transducer so that ultrasonic vibrations may be transmitted into the delay line from the ultrasonic transducer in a first direction, the delay line includes a first section and a second section; the first and second sections forming an interface that is substantially perpendicular to the first direction; and the second section including a surface for coupling with a material to be investigated. The probe can be used to measure a thickness of a coating on a substrate by transmitting a signal in a first direction from the transducer into the delay line; measuring a time $t_1$ for a first portion of the signal to travel round trip from the transducer and the interface; using the measured time $t_1$ to calculate an expected time $t_2$ for a second portion of the signal to travel round trip from the transducer to an opposite face of the delay line; measuring a time $t_3$ that it takes for a third portion of the signal to travel round trip from the transducer and an interface between the coating and the substrate; and calculating a thickness of the coating based on a difference between the time $t_2$ and the time $t_3$.

5 Claims, 6 Drawing Sheets

DELAY LINE FOR AN ULTRASONIC PROBE AND METHOD OF USING SAME

This application is a divisional of application Ser. No. 08/392,507, filed Feb. 23, 1995 U.S. Pat. No. 5,777,230.

BACKGROUND OF THE INVENTION

1. Field of the Invention

The present invention relates to a probe for an ultrasonic gauge, and in particular, to a probe having a delay line construction that enables probe measurements to be adjusted to compensate for changes in temperature of the delay line.

2. Discussion of Related Art

Ultrasound provides an ideal physical mechanism to investigate surface flaws or the thickness of coatings on substrata with acoustically different properties. When a coating is applied to a substrate that has acoustic properties that are different from those of the coating, an acoustic coating/substrate interface is created. At such an interface or at a flaw, an ultrasonic vibration will be partially reflected.

For example, an ultrasonic vibration, also known as an impulse, can be transmitted into a coating using a resonant piezo element transducer. The same transducer can also be setup to "listen" for echoes created when the impulse reflects from the interface of the coating and substrate back to the transducer. The output of the transducer can be recorded for a known period after the impulse has been transmitted. This period is defined as an echo window. The echo window is defined to overlap with the time of expected echoes of interest.

By analyzing the echo recorded during the echo window, it is possible to determine the location of a flaw or an interface between the coating and the substrate. The thickness of the coating can be determined if the velocity of sound within the coating material and the time of the interface echo are known. In other words, the thickness of the coating can be determined by multiplying the velocity of the vibration through the coating material times the time for the vibration to enter the coating, reflect off the interface, and exit the coating, and dividing that product by two.

$$Thickness = (Velocity \times Time)/2$$

The resolution of the derived thickness is limited by the temporal resolution of the sampled echo. Improvements in the resolution of the sampled echo will directly improve the resolution of the derived thickness.

In U.S. patent application, Ser. No. 08/127,529, a detailed description of an improved ultrasonic gauge is disclosed. The subject matter of U.S. patent application, Ser. No. 08/127,529, is hereby incorporated herein by reference.

When using ultrasound to investigate near surface flaws, such as in the case with thin coatings, a delay line or stand off block is frequently required to separate the noise associated with the transducer excitation signal. Thus the practical investigation of near surface flaws requires the use of such an acoustic delay line.

The determination of the reflection times for closely spaced flaws represents a difficulty when the flaw or coating/substrate interfaces are less than one wavelength of the frequency of investigation. To overcome this limitation, several techniques can be employed, such as increasing the frequency of the ultrasonic impulse or using relatively low frequencies coupled with the use of matched delay lines.

With a high frequency broad band transducer, it is possible to separate surface echoes from flaw echoes. A 100 MHz ultrasonic signal has a wavelength of approximately 10.6 $\mu$m in polystyrene, whereas a 10 MHz signal has a wave length of 106 $\mu$m. Clearly the 100 MHz signal is able to resolve finer detail.

The use of a delay line matched to the coating material under investigation allows the use of lower frequencies by eliminating the need to separate the surface entry echo from the echo from a flaw or the far side of the coating. It is advantageous to use lower frequencies for several reasons, among them being lower instrumentation costs and complexity as a result of the reduced bandwidth requirements. In addition, the transducer construction is made considerably easier.

When constructing matched delay lines the acoustic properties of the delay element may be less than ideal since material characteristics are imposed by the coating characteristics under investigation. Consider a thin polymer based coating applied to a dissimilar substrate. Since the coating is a polymer, the delay line must also be of a similar material. The use of a matched delay line requires that the delay tip reflection be known so that it can be distinguished from the flaw reflection to determine thickness or flaw location. Typically the delay tip reflection can be obtained by removing the transducer from the test piece and measuring the time for a vibration to travel from the transducer to the delay line material/air interface, and back to the transducer again. This propagation time is retained for future use and is commonly referred to as the probe "zero". When the delay line material is coupled to the test piece, a measurement of the time for a vibration to travel from the transducer to the far side of the test piece, and back to the transducer again is obtained. When the probe "zero" time is subtracted from the time obtained from the test piece, the thickness of the test piece can be readily calculated.

One difficulty with such a technique is that the probe "zero" time can change with variations in temperature due to the velocity changes in the delay material. Furthermore, delay lines of typical construction are relatively long compared to the coating thickness. As a result the errors associated with the temperature related velocity change in probe "zero" temporal location are significant.

When measuring very thin coatings, small changes in temperature, such as those brought about by simply touching the transducer can cause measurement errors on the order of 100% of the coating thickness itself.

One prior art method of compensating for such temperature changes is disclosed in U.S. Pat. No. 4,437,332, issued to Pittaro. Pittaro discloses a method of calibrating an instrument by measuring the time required for a vibration to travel round trip to and from a calibration specimen of a known thickness. The system then computes an offset time value to compensate the system for changes in the velocity of propagation. The offset time value is then used to measure objects of unknown dimension. However, the system can only be calibrated by applying the delay line to a calibration specimen of a known thickness. Thus, calibrating the system is time consuming and cannot easily be done before each measurement. As a result, the delay line may experience changes in the temperature, as a result of handling or other causes, between calibrations that will negatively affect measurements.

The delay line disclosed by Pittaro also includes a notch, wherein the time for a signal to travel back and forth between a transducer and the notch can be used to identify the delay line. However, inaccurate identifications may occur if the delay line experiences temperature changes that affect the velocity of propagation of the signal in the delay line.

SUMMARY AND OBJECTS

It is an object of the present invention to provide a delay line for use in ultrasonic investigations, wherein through a simple procedure, the system using the delay line can be calibrated to account for temperature induced changes, such as temperature induced changes, in the delay line.

It is a further object of the present invention to teach a technique and probe construction that allows the use of a matched delay line transducer to measure near surface flaws, such as in thin coatings, or coating thicknesses by providing a temperature compensated delay tip temporal signal for use as a compensated probe zero signal to be used in calculating thickness.

It is yet another object of the present invention to provide a delay line that includes internal reflectors such that the relative amplitudes of the reflections from the internal reflectors can be used to uniquely identify the delay line and thus the transducer that is connected to it. It is advantageous to be able to automatically identify a transducer so that a common instrument can be used for a number of different applications where unique probe configurations are required. An operator of such an instrument need only replace the transducer and the instrument could adapt program flow appropriately.

The foregoing objects, as well as other advantages, may be achieved by one or more of the devices and methods described hereinafter.

An ultrasonic probe includes an ultrasonic transducer; a delay line acoustically coupled to said transducer so that ultrasonic vibrations may be transmitted into said delay line from said ultrasonic transducer in a first direction, said delay line includes a first section comprised of a first material and a second section comprised of a second material; said first and second sections forming an interface that is substantially perpendicular to said first direction; and said second section including a surface for coupling with a material to be investigated.

Another ultrasonic probe includes an ultrasonic transducer; a delay line acoustically coupled to said transducer so that ultrasonic vibrations may be transmitted into said delay line from said ultrasonic transducer in a first direction, said delay line includes a first section and a second section; a partial reflector sandwiched between said first and second sections and arranged substantially perpendicular to said first direction; and said second section including a surface for coupling with a material to be investigated.

A method of measuring a thickness of a coating on a substrate includes transmitting a signal in a first direction from a transducer into a delay line coupled to said transducer, wherein said delay line includes means for reflecting at least a first portion of said signal at a known distance from said transducer; measuring a time $t_1$ for the first portion of the signal to travel round trip from the transducer and the reflecting means; using said measured time $t_1$ to calculate an expected time $t_2$ for a second portion of the signal to travel round trip from said transducer to an opposite face of said delay line; measuring a time $t_3$ that it takes for a third portion of the signal to travel round trip from said transducer and an interface between said coating and said substrate; and calculating a thickness of said coating based on a difference between the time $t_2$ and the time $t_3$.

And, a method of identifying a delay line for an ultrasonic transducer, comprises the steps of transmitting an ultrasonic vibration in a first direction from a transducer into a delay line acoustically coupled to said transducer, wherein said delay line includes a reflector at a known distance from said transducer; measuring a time $t_1$ for a vibration to travel round trip from the transducer and the reflector; measuring a time $t_2$ for a vibration to travel round trip from the transducer and an opposite face of said delay line; calculating a ratio based on $t_1$ and $t_2$; and using said calculated ratio to identify the delay line.

Another method of identifying a delay line for an ultrasonic transducer, comprising the steps of transmitting an ultrasonic vibration in a first direction from a transducer into a delay line acoustically coupled to said transducer, wherein said delay line includes an interface at a known distance from said transducer; measuring a first reflection amplitude of a vibration that has reflected from the interface; measuring a second reflection amplitude of a vibration that has reflected from an opposite face of said delay line; calculating a ratio based on said first and second reflection amplitudes.

DETAILED DESCRIPTION OF PREFERRED EMBODIMENTS

The present invention relates to a gauge for measuring the thickness of coatings on substrata. It is intended to resolve a prior art problem created by changes in the propagation velocity of ultrasonic impulses through a delay line caused by changes in the temperature of the delay line.

Figure 1:
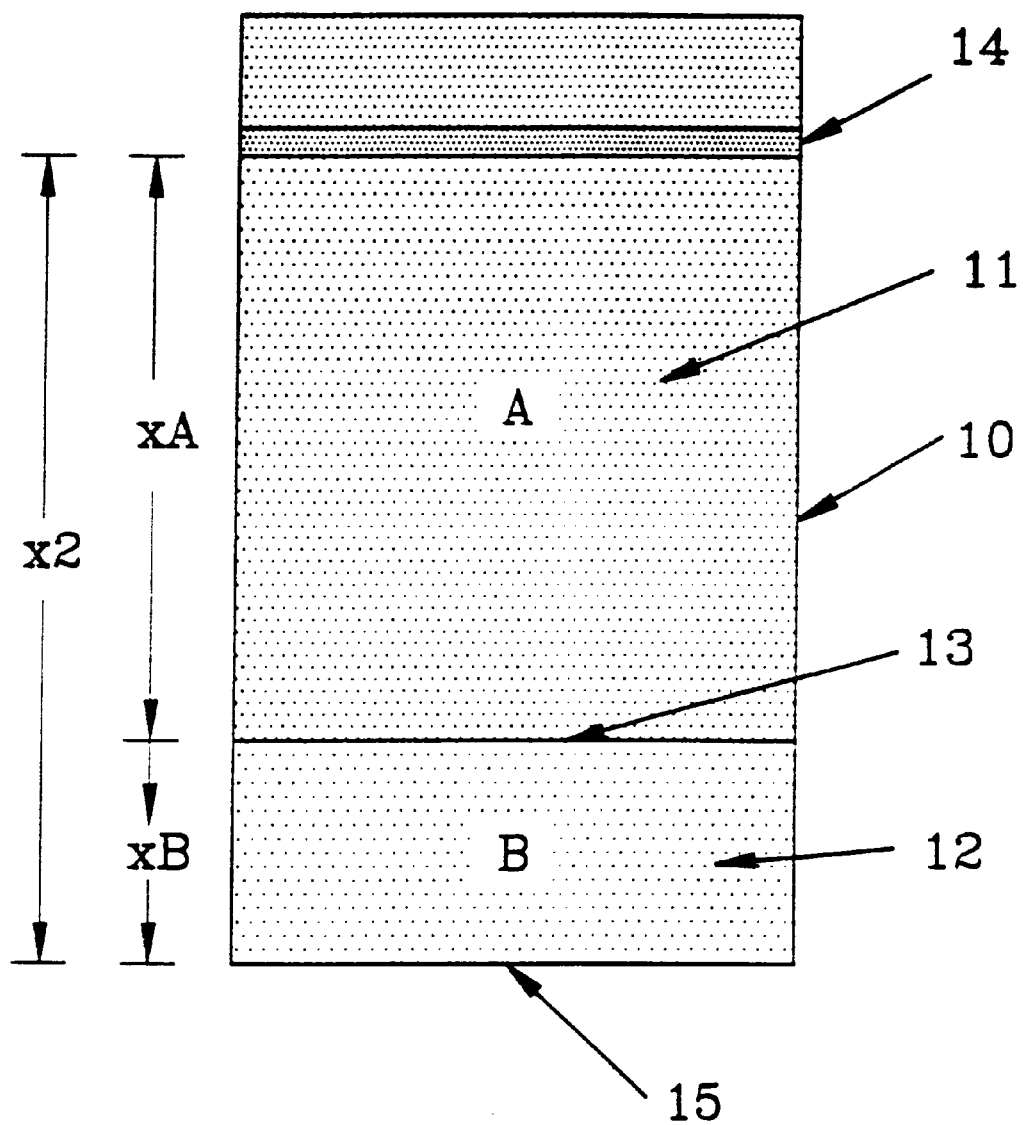
FIG. 1 is a representational view of a delay line according to the present invention.

The geometry of the materials and the acoustic properties of the materials to be used in a representative delay element of the present invention is illustrated in FIG. 1, which is a representative view of a delay line 10 for use with an ultrasonic transducer 14. A first section 11 of the delay line 10 is made from a material A, and forms an interface between the transducer 14 and the delay line 10. The material A may be polystyrene, an acrylic resin, or any other suitable material.

A second section 12 of the delay line 10 is made from a material B, and is attached to the first section 11 at an interface 13. The material B may be polystyrene, an acrylic resin, or any other suitable material.

The A/B interface 13 forms an acoustic marker of known acoustic properties. The second section 12 includes a face 15, opposite the interface 13, which is applied to surfaces to be investigated.

Figure 2:
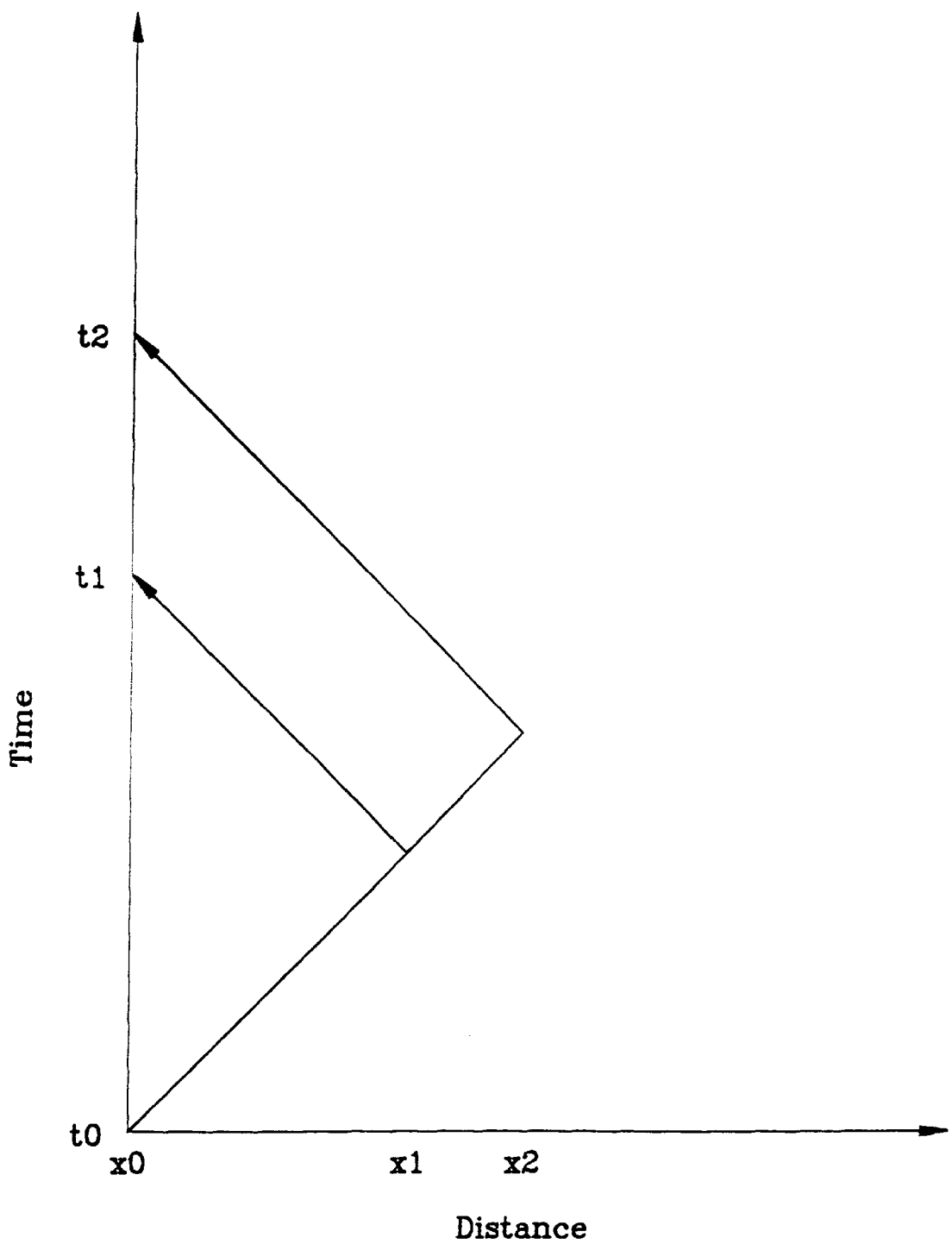
FIG. 2 is a timing diagram for the delay line shown in FIG. 1.

When excited by an electrical signal at time $t_0$, the transducer 14 resonates at its fundamental frequency. The resultant ultrasonic vibration propagates through the delay line 10. At the A/B interface 13, the ultrasonic vibration is partially reflected. The time diagram of FIG. 2 illustrates the vibration arrival time $t_1$ at the transducer 14 of an ultrasonic reflection that is partially reflected from the A/B interface 13. At time $t_1$ the partially reflected vibration is detected by the transducer 14. The vibration is converted by the transducer into an electrical signal that can be easily sampled and stored in a digital computer or converted by some appropriate means into a time dependent signal that represents the time $t_1-t_0$.

Simultaneous to the partial reflection at the A/B interface 13, a portion of the vibration is transmitted through the A/B interface 13 and into the second section 12 of the delay line 10. That portion of the vibration then propagates through the second section 12 until it reaches the delay line face 15.

Depending on the surface, if any, that is in contact with the face 15, a reflection may or may not occur off the face 15. If the delay line 10 is not in contact with a surface, i.e., the material contacting the face 15 is air, another partial reflection will occur at the face 15 and the vibration will propagate back towards the transducer 14, with some residual reflection and transmitting at the A/B interface 13 and eventually arriving at the transducer 14 at time $t_2$.

Figure 3:
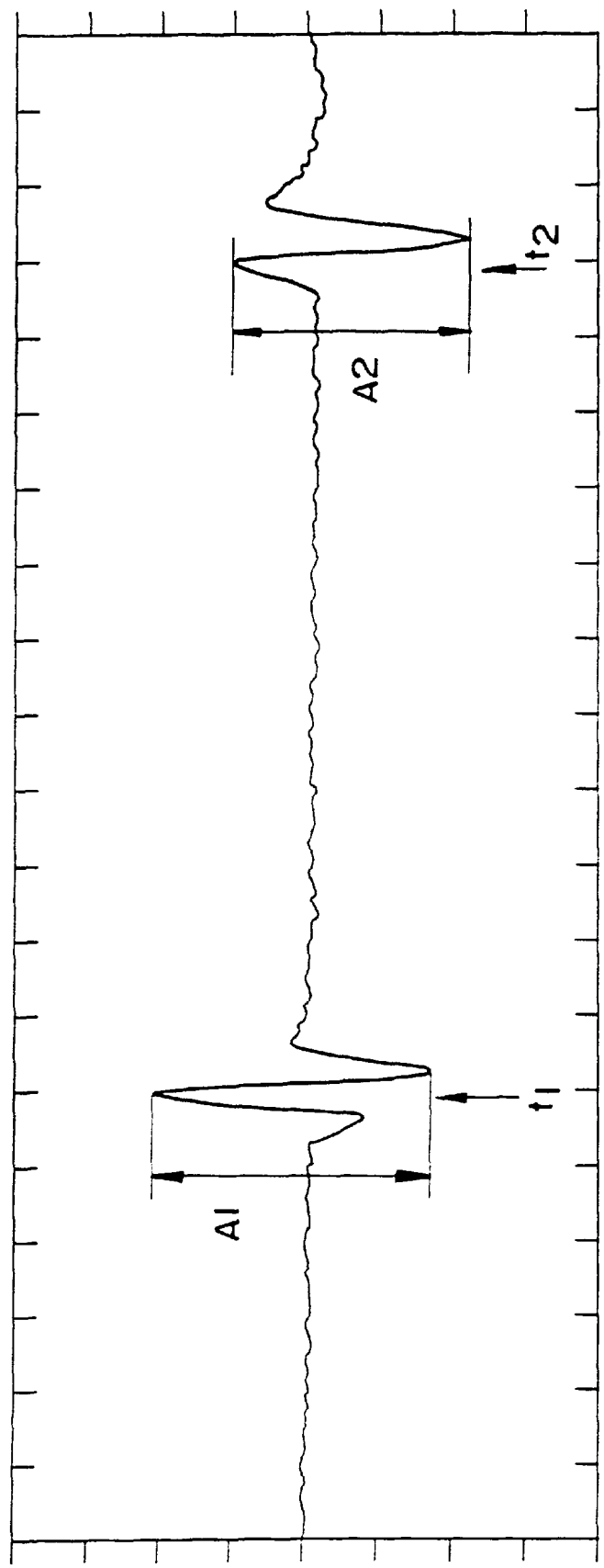
FIG. 3 is a scan of the timing diagram of FIG. 2 showing the amplitude of reflections.

FIG. 3 illustrates the relative strength, i.e., amplitude, of the reflected vibrations that are illustrated in FIG. 2. As shown in FIG. 3, a ratio of the amplitudes (A) of the echoes reflected from the A/B interface 13 and the face 15 can be calculated. The calculated ratio (e.g., A2/A1) can be used to identify a probe.

For example, each delay line may be constructed with a specific or unique combination of materials (A and B) and section lengths (see xA and xB in FIG. 1). A probe could thus be uniquely identified by appropriate choice of materials A and B. Alternatively, the lengths xA and/or xB could be changed to create a unique delay line. The ratio of xA/xB could then uniquely identify a probe.

Figure 5:
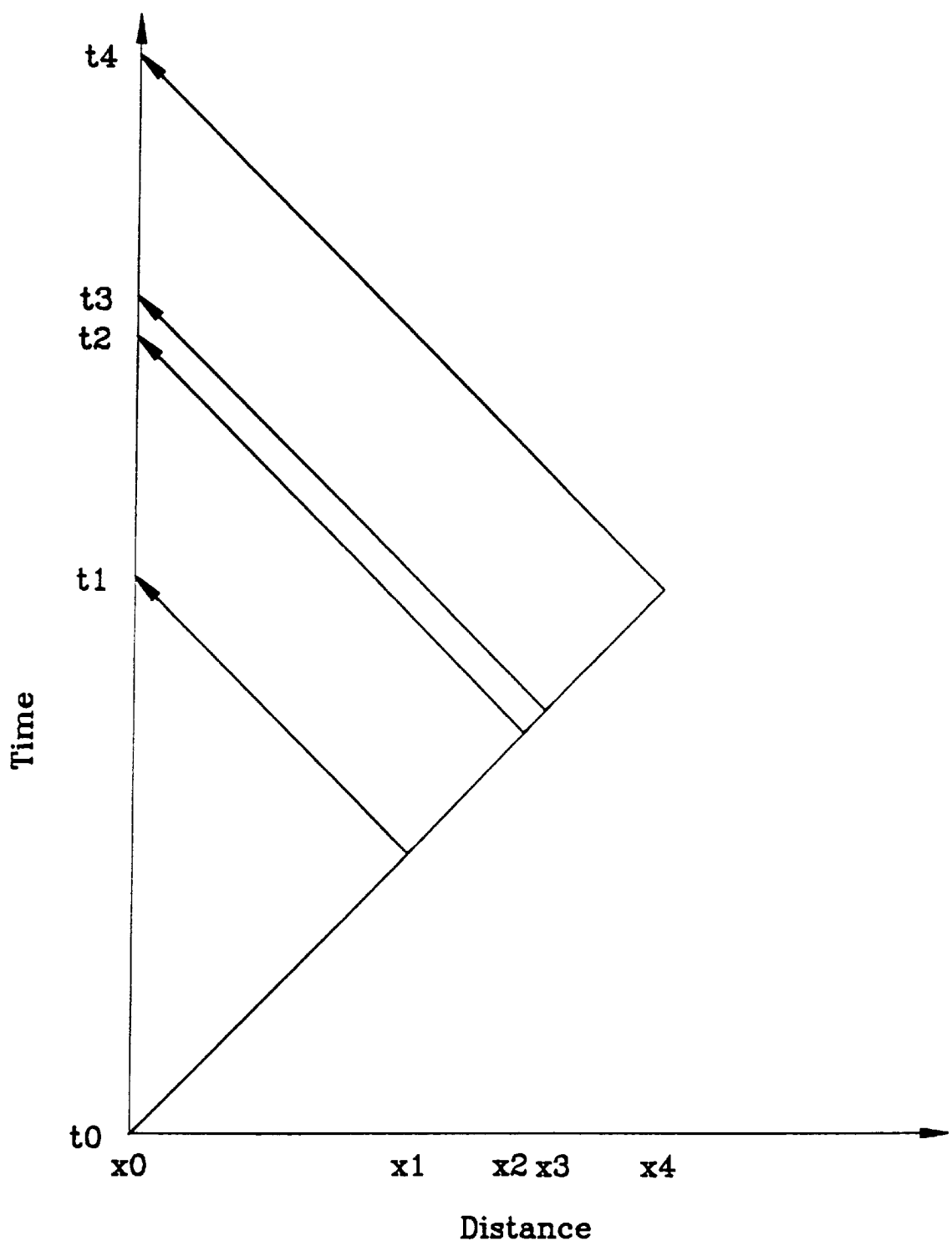
FIG. 5 is a timing diagram for the delay line shown in FIG. 4.
Figure 6:
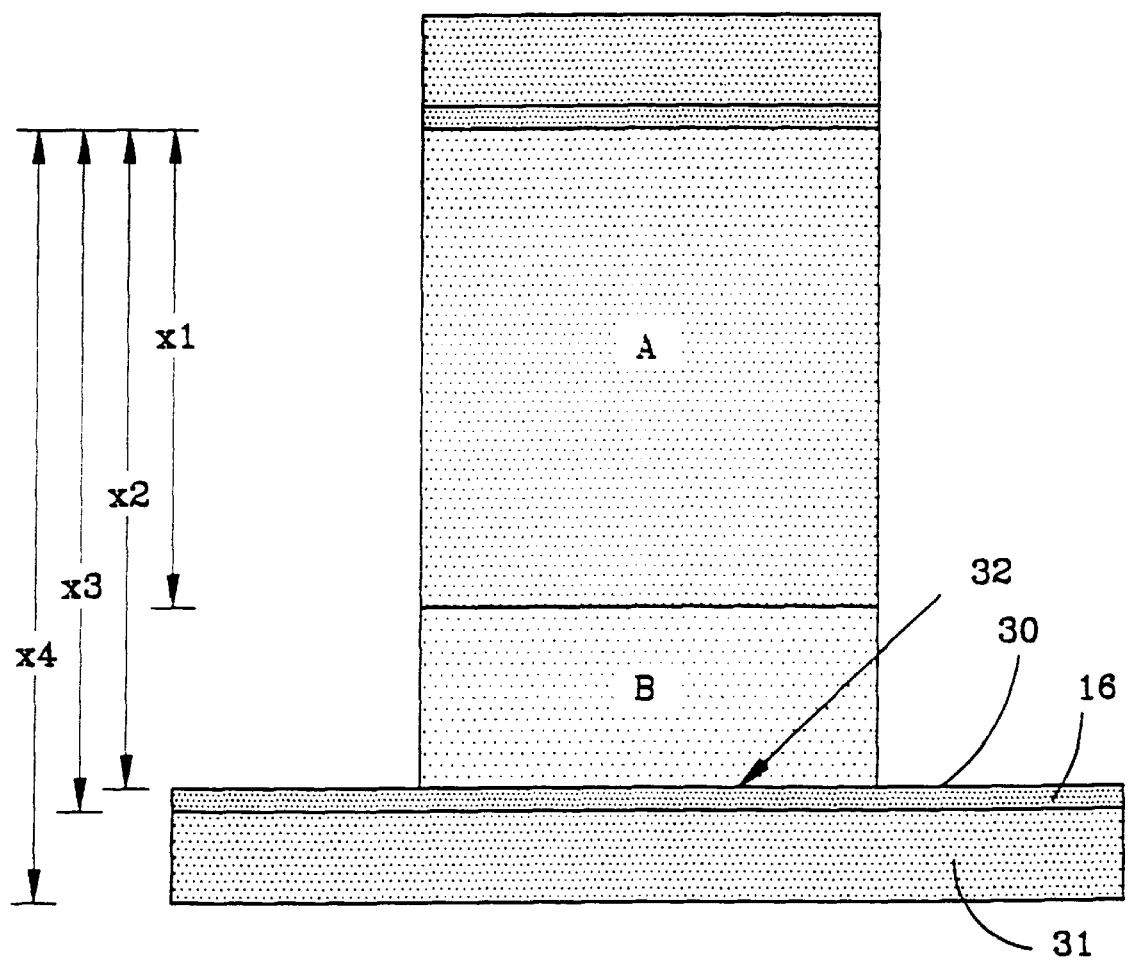
FIG. 6 illustrates an application of the delay line of FIG. 1.

Turning attention now to FIG. 6, the delay line of FIG. 1 is acoustically coupled to a thin coating material 30 on a base 31 of dissimilar material. FIG. 5 illustrates a timing diagram generated as a result of propagating an ultrasonic vibration from the transducer 14 through the delay line 10 and the coating 30. In FIG. 5, $t_1$ represents the time at which a vibration reaches the transducer 14 after reflecting off the A/B interface 13. Time $t_2$ represents the time at which a vibration reaches the transducer 14 after reflecting off the face 15. Time $t_3$ represents the time at which a vibration reaches the transducer 14 after reflecting off an interface 16 between the coating 30 and the substrate 31. And, time $t_4$ represents the time at which a vibration reaches the transducer 14 after reflecting off the far side of the substrate 31.

As will be explained with reference to FIG. 5, it is advantageous to know the location in time of the delay tip echo (i.e., time $t_2$) when the material of the coating 30 and the material B comprising the second section 12 are the same or acoustically similar.

The difference between time $t_3$ and time $t_2$ represents the time required for a round-trip for a vibration to pass into the coating 30, reflect off the coating/substrate interface 16, and pass back out of the coating into the delay line 10. If the velocity of propagation of the ultrasonic vibration through the material of the coating 30 is known, the thickness $T_c$ of the coating 30 can be determined by the following formula:

$$T_c = (V_{30})(t_3-t_2)/2,$$

where $V_{30}$ represents the velocity of propagation in material 30. If the material B of the second section 12 is similar to or the same as the material of the coating 30, there may be very little reflection obtained from the interface between the two. With no reflection at that interface, time $t_2$ is unknown. Conventional techniques rely on knowing time $t_2$ in order to measure the distance $x_3-x_2$ (see FIG. 5). Conventional techniques typically measure the time $t_2$ when no material is coupled to the delay line 10. This procedure is known as zeroing the probe. As such, a zero reference is determined for the delay line 10. Assuming that time $t_2$ is constant this technique works well.

However, the velocity of propagation through a material is dependent on the temperature of the material, among other variables, as related by v=f(t, . . . ). As a result, time $t_2$ is dependent on temperature. Small changes in temperature caused simply by touching the probe has been shown to cause significant errors in the measured thickness $x_3-x_2$.

Using the disclosed techniques it is possible to compensate for temperature effects by measuring the time $t_1$ for the known distance between the transducer 14 and the A/B interface 13 (xA or x1) and then calculating the temperature as follows:

$$temp=f(x1, t1, \ldots)$$

Knowing the temperature allows for the prediction of $t_2$ using the following expressions:

$$t_2=(2)(x1)/v_A+(2)(x2-x1)/v_B$$

$$t_2=t_1+(2)(x2-x1)/f(v1(temp)),$$

wherein $v_A$ is the velocity of propagation through material A, $v_B$ is the velocity of propagation through material B, x1 is the length of the first section 11, x2 is the length of the first and second sections combined, and $f(v_A(temp))$ is a function for calculating $v_B$ as a function of temperature.

By defining $v_B$ in terms of $v_A$, $t_2$ can be determined for all values of $V_A$ within a defined operating range for the delay line. Within defined temperature and frequency limits, $v_B$ can be estimated by the ratio of $v_A$ to $v_B$.

$$v_B(temp_x)=v_A(temp_x)(v_B(temp_0)/v_A(temp_0))$$

A preferred embodiment of a delay line, as illustrated in FIG. 1, may be constructed of the following properties:

Material A=Acrylic resin

Material B=Polystyrene

Frequency of transducer=10 MHz xA=213 mils xB=110 mils.

According to one embodiment of the present invention, the system can be designed so that the foregoing analysis is conducted before every coating thickness measurement. Specifically, when a thickness coating measurement is requested by the activation of an appropriate switch, an ultrasonic signal is generated. Based on the ultrasonic signal, times $t_1$ and $t_3$ are measured, velocity $v_1$ is calculated based on time $t_1$, velocity $v_2$ is estimated based on $v_1$, and time $t_2$ is calculated based on $v_1$ and $v_2$. The thickness of the coating is then calculated based on a difference between $t_3$ and $t_2$. Thus, the system is essentially adjusted for temperature changes immediately before each measurement is taken.

Figure 4:
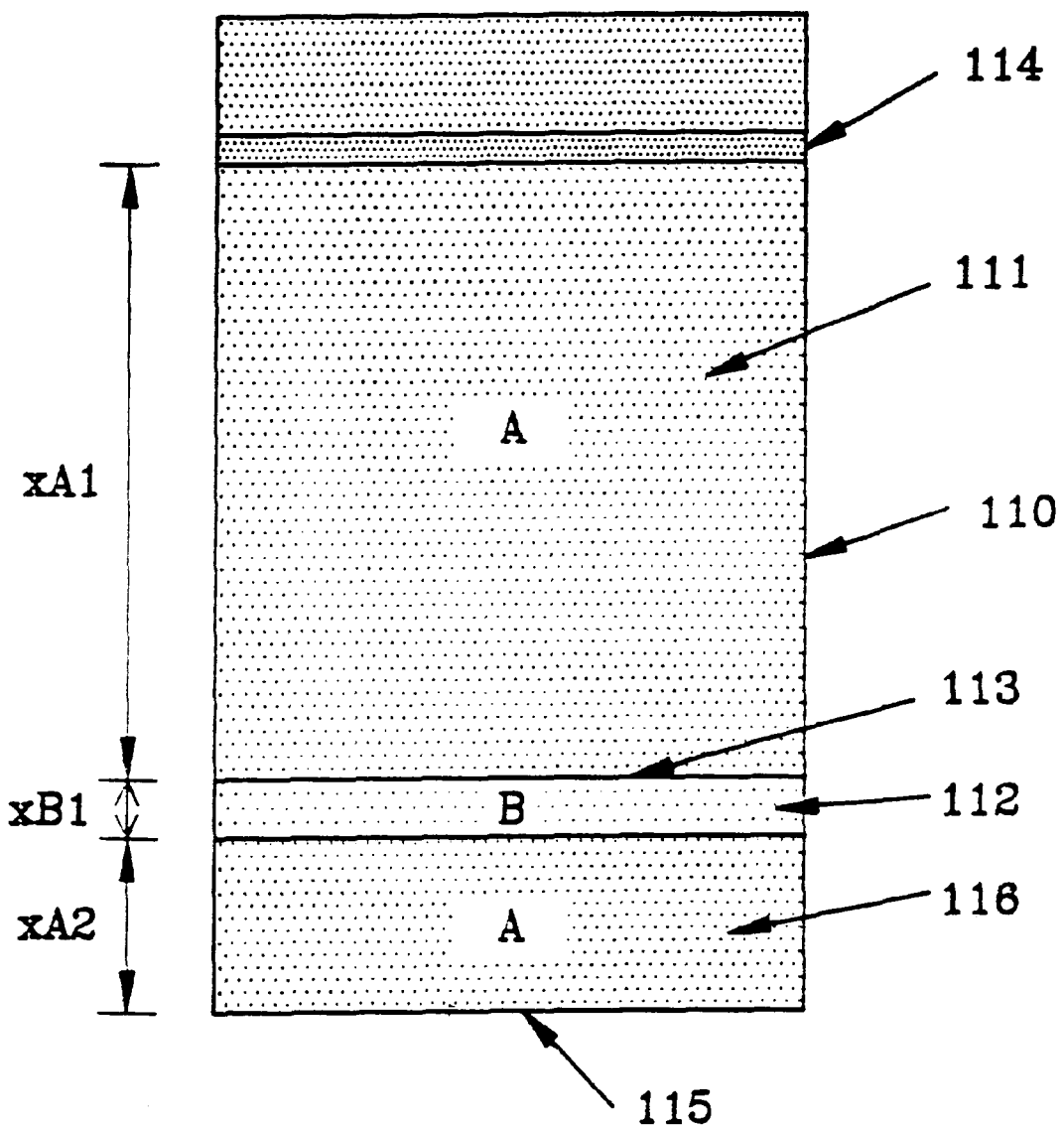
FIG. 4 is a representational view of an alternative delay line according to the present invention.

An alternate embodiment of a delay line according to the present invention is constructed as illustrated in FIG. 4. It may be advantageous to construct a delay line as shown in FIG. 4 to simplify the calculations required to predict the probe zero. In addition the configuration of FIG. 4 enables the ratio of the amplitudes of the reference echo and the delay tip echo to be more closely matched.

In the preferred embodiment of FIG. 4, a first section 111 is made from a material A, and is coupled to a transducer 114. A second section 112, which is made from material B, is comparatively short, and is connected to the first section 111 along an interface 113. A third section 116 is connected to the second section 112. The third section 116 may be made from the same material A as the first section 111, or any other suitable material. A face 115 of the delay line 110 may be coupled to a surface to be investigated. In a preferred embodiment, the following parameters apply:

Material A=Polystyrene

Material B=Aluminum xA1=275 mils xB1=0.5 mils xA2=50 mils

The second section 112 is essentially a metal foil of minimal thickness. Thus, in the preferred embodiment of FIG. 4, the time $t_2$ for a round trip between the transducer 114 and the delay tip 115 can be estimated as follows:

$$t2 = t1 + t1(xA2/xA1)$$

To facilitate automatic probe identification, the ratio of the time ($t_1$) of the reflection obtained from the interface between the first section 111 and the second section 112, and the time ($t_2$) of the reflection obtained from the end of the delay line can be measured, since such a ratio corresponds to the ratio of the lengths of the respective sections. By altering the material used as material B a different ratio can also be obtained. Alternatively, the length of xA2 can be changed. Thus the ratio of xA2/xA1 can uniquely identify a probe.

In addition, the probe can be identified by comparing the amplitude A2 (of the reflection obtained from the end of the delay line) to the amplitude A1 (of the reflection obtained from the interface between the first section 111 and the second section 112. See FIG. 3.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An ultrasonic probe for calculating a thickness of a coating on a substrate, comprising:

an ultrasonic transducer;

a delay line acoustically coupled to said transducer so that an ultrasonic signal may be transmitted into said delay line from said ultrasonic transducer in a first direction;

means for reflecting at least a first portion of said signal at a known distance from said transducer, said reflecting means located within the delay line;

means for measuring a first time for the first portion of the signal to travel round trip from the transducer to the reflecting means;

means for measuring a second time for a second portion of the signal to travel round trip from the transducer to an interface between the coating and the substrate; and means for using said first time to calculate a temperature adjusted value which can be used to calculate the thickness of the coating based on the second time.

2. The ultrasonic probe of claim 1, wherein the adjusted value represents a location of an interface between the delay line and the coating.

3. An ultrasonic probe for calculating a thickness of a coating on a substrate, comprising:

an ultrasonic transducer;

a delay line acoustically coupled to said transducer so that an ultrasonic signal may be transmitted into said delay line from said ultrasonic transducer in a first direction;

means for reflecting at least a first portion of said signal at a known distance from said transducer, said reflecting means being located within the delay line;

means for measuring a time for the first portion of the signal to travel round trip from the transducer to the reflecting means and back; and means for calculating a temperature compensation value based on said time which can be used to obtain temperature compensated coating thickness readings that account for temperature changes in the probe.

4. A method of using an ultrasonic probe for calculating a thickness of a coating on a substrate, comprising:

acoustically coupling a delay line to an ultrasonic transducer so that an ultrasonic signal may be transmitted into said delay line from said ultrasonic transducer in a first direction;

reflecting at least a first portion of said signal at a known distance from said transducer with a reflector located within the delay line;

measuring a time for the first portion of the signal to travel round trip from the transducer to the reflecting means and back;

calculating a temperature compensation value based on said time; and using the temperature compensation value to obtain temperature compensated coating thickness readings that account for temperature changes in the probe.

5. The ultrasonic probe of claim 3, wherein the reflecting means includes a planar surface.

* * * * *